(12) United States Patent
Wannerberger et al.

(10) Patent No.: US 8,119,161 B2
(45) Date of Patent: Feb. 21, 2012

(54) BLISTER PACK AND SOLID DOSAGE FORM THEREFOR

(75) Inventors: Kristin Wannerberger, Lund (SE); Lars Anders Ragnar Nilsson, Lund (SE)

(73) Assignee: Ferring BV, Hoofddorp (NL)

(*) Notice: Subject to any disclaimer, the term of this patent is extended or adjusted under 35 U.S.C. 154(b) by 458 days.

(21) Appl. No.: 10/519,715

(22) PCT Filed: Nov. 12, 2004

(86) PCT No.: PCT/EP2004/052940
§ 371 (c)(1),
(2), (4) Date: Aug. 9, 2005

(87) PCT Pub. No.: WO2005/046646
PCT Pub. Date: May 26, 2005

(65) Prior Publication Data
US 2007/0117759 A1    May 24, 2007

(30) Foreign Application Priority Data
Nov. 13, 2003 (EP) .................................... 03025959

(51) Int. Cl.
A61K 9/14 (2006.01)
A61K 9/20 (2006.01)
A61K 9/26 (2006.01)

(52) U.S. Cl. .................. 424/489; 424/464; 424/470

(58) Field of Classification Search ........................ None
See application file for complete search history.

(56) References Cited

U.S. PATENT DOCUMENTS

| | | | |
|---|---|---|---|
| 4,263,283 A | 4/1981 | Cort | |
| 4,285,858 A | 8/1981 | Cort et al. | |
| 4,731,360 A | 3/1988 | Alexander et al. | |
| 4,764,378 A | 8/1988 | Keith et al. | |
| 4,863,737 A | 9/1989 | Stanley et al. | |
| 5,047,398 A | 9/1991 | Hagstam et al. | |
| 5,298,256 A * | 3/1994 | Flockhart et al. | 424/435 |
| 5,466,464 A * | 11/1995 | Masaki et al. | 424/434 |
| 5,482,931 A | 1/1996 | Harris et al. | |
| 5,498,598 A | 3/1996 | Harris et al. | |
| 5,500,413 A | 3/1996 | Larsson et al. | |
| 5,596,078 A | 1/1997 | Andersson et al. | |
| 5,674,850 A | 10/1997 | Larsson et al. | |
| 5,698,516 A | 12/1997 | Nilsson et al. | |
| 5,726,287 A | 3/1998 | Andersson et al. | |
| 5,763,398 A | 6/1998 | Bengtsson et al. | |
| 5,763,405 A | 6/1998 | Fjellestad-Paulsen et al. | |
| 5,763,407 A | 6/1998 | Larsson et al. | |
| 5,780,434 A | 7/1998 | Fjellestad-Paulsen et al. | |
| 5,849,322 A | 12/1998 | Gutniak et al. | |
| 5,922,680 A | 7/1999 | Fjellestad-Paulsen et al. | |
| 5,976,577 A | 11/1999 | Green et al. | |
| 5,985,835 A | 11/1999 | Larsson et al. | |
| 5,990,273 A | 11/1999 | Andersson et al. | |
| 6,143,722 A | 11/2000 | Melin et al. | |
| 6,248,363 B1 | 6/2001 | Patel et al. | |
| 6,264,981 B1 | 7/2001 | Zhang et al. | |
| 6,348,486 B1 | 2/2002 | Argentieri et al. | |
| 6,509,040 B1 | 1/2003 | Murray et al. | |
| 6,664,249 B1 | 12/2003 | Ashworth et al. | |
| 6,693,082 B2 | 2/2004 | Alonso et al. | |
| 6,746,678 B1 | 6/2004 | Shapiro | |
| 7,018,653 B2 | 3/2006 | Wannerberger et al. | |
| 7,022,340 B2 | 4/2006 | Lomryd et al. | |
| 7,060,708 B2 | 6/2006 | Piccariello et al. | |
| 7,074,781 B2 | 7/2006 | Ashworth et al. | |
| 7,094,545 B2 | 8/2006 | Lomryd et al. | |
| 7,176,195 B2 | 2/2007 | Ashworth et al. | |
| 7,405,203 B2 | 7/2008 | Fein | |
| 7,560,429 B2 | 7/2009 | Nilsson et al. | |
| 7,560,454 B2 | 7/2009 | Ashworth et al. | |
| 7,579,321 B2 | 8/2009 | Fein | |
| 7,947,654 B2 | 5/2011 | Nilsson et al. | |
| 2003/0119728 A1 | 6/2003 | Scheidl et al. | |
| 2004/0138098 A1 * | 7/2004 | Fein | 514/2 |
| 2005/0232997 A1 | 10/2005 | Nilsson et al. | |
| 2006/0025387 A1 | 2/2006 | Hochman | |
| 2006/0193825 A1 | 8/2006 | Musso et al. | |
| 2006/0240068 A1 | 10/2006 | Lomryd et al. | |
| 2006/0241172 A1 | 10/2006 | Zhou et al. | |
| 2006/0252696 A1 | 11/2006 | Lomryd et al. | |
| 2007/0117759 A1 | 5/2007 | Wannerberger et al. | |

(Continued)

FOREIGN PATENT DOCUMENTS

AU    2002337419 A1    11/2003

(Continued)

OTHER PUBLICATIONS

Applicants' admission on the record; see p. 2, lines 3-10 of the specification.*
Remington: The Science and Practice of Pharmacy (19th Ed.); Ch. 85, pp. 1492-1493 (1995).*
U.S. Patent Documents—None.*
H. Seager; J. Pharm. Pharmacol.; 50 (4): pp. 375-382; 1998.*
Minirin®—Tablet package information (Ferring) (4 pgs.).
Final Office Action dated Nov. 15, 2007 in U.S. Appl. No. 10/513,437 (12 pgs.).
Grossman, A. et al., "Two new nodes of desmopressin (DDAVP) administration", *British Medical Journal*, May 17, 1980, p. 1215, XP00226048.

(Continued)

*Primary Examiner* — Robert A Wax
*Assistant Examiner* — Jeffrey T Palenik
(74) *Attorney, Agent, or Firm* — Foley & Lardner LLP

(57) ABSTRACT

The present invention relates to a blister pack for pharmaceutical use comprising blisters containing a solid dosage form of desmopressin, or a pharmaceutically acceptable salt thereof, and to said solid dosage form. In one embodiment it specifically relates to a blister pack for pharmaceutical use comprising blisters containing a solid dosage form of desmopressin, or a pharmaceutically acceptable salt thereof, in association with a pharmaceutically acceptable adjuvant, diluent and/or carrier, wherein said solid dosage form is adapted to prevent moisture related degradation of said desmopressin.

11 Claims, No Drawings

U.S. PATENT DOCUMENTS

| | | | |
|---|---|---|---|
| 2008/0274951 | A1 | 11/2008 | Fein |
| 2009/0005432 | A1 | 1/2009 | Fein |
| 2010/0273709 | A1 | 10/2010 | Aston et al. |

FOREIGN PATENT DOCUMENTS

| | | | |
|---|---|---|---|
| AU | 2003233118 B2 | | 11/2003 |
| EP | 0 517 211 A1 | | 12/1992 |
| EP | 1 153 616 A1 | | 11/2001 |
| GB | 1 548 022 | | 7/1979 |
| GB | 2 111 184 A | | 6/1983 |
| GB | 2 111 423 A | | 7/1983 |
| GB | 2 114 440 A | | 8/1983 |
| WO | WO 85/02119 A | | 5/1985 |
| WO | WO 03/094886 | * | 11/1993 |
| WO | WO-94/12142 A1 | | 6/1994 |
| WO | WO 95/01185 A | | 1/1995 |
| WO | WO-00/36353 A1 | | 6/2000 |
| WO | WO 00 44351 A1 | | 8/2000 |
| WO | WO-0044351 | | 8/2000 |
| WO | WO-00/59423 | | 10/2000 |
| WO | WO 00 59423 A1 | | 10/2000 |
| WO | WO-00-61117 | | 10/2000 |
| WO | WO 00 61117 A1 | | 10/2000 |
| WO | WO 01/60394 A | | 8/2001 |
| WO | WO-02/074286 A1 | | 9/2002 |
| WO | WO 03 094885 A | | 11/2003 |
| WO | WO 03/094886 A | | 11/2003 |
| WO | WO-2004/041153 A2 | | 5/2004 |
| WO | WO-2005/046707 A1 | | 5/2005 |

OTHER PUBLICATIONS

Doctoral Dissertation, "Absorption and Metabolism of Neurophypophyseal Hormones, with special reference to Desmopressin (dDAVP), in Human Tissue and after Various Routes of Administration", (Fjellestad-Paulsen, Anne M.) May 25, 1996.

Trinh-Trang-Tan et al. "Regulation of UT-A2 Protein in vivo and in vitro", Journal of the American Society of Nephrology, (Sep. 2000) vol. 11, Program and Abstract Issue, pp. 23A.

Laczi, F. et al., "Effects of vasopressin analogues (DDAVP, DVDAVP) in the form of sublingual tablets in central diabetes insipidus", *International Journal of Clinical Pharmacology, Therapy and Toxicology*, vol. 18, No. 12, pp. 63-68 (1980).

U.S. Appl No. 12/487,116, filed Jun. 2009, Nilsson et al.

U.S. Appl. No. 12/224,437, filed Aug. 2008, Aston

"Minirin Nasal Spray". Ferring Pharmaceuticals. Internet document <<http://www.medsafe.gov/nz/Consumers/CMI/m/MiniriNSpray.htm>&g- t; May 3, 2001; accessed Sep. 15, 2008; 4 pages.

Wolfson Philip et al. (1979) "Mechanism of Vasopressin Inhibition of Pancreatic Secretion", American Journal of Gastroenterology, vol. 71, No. 5, pp. 490-495.

Jahr S Jonathan et al. (1992) "Effect of Desmopressin Acetate on Hindlimb Perfusion Pressure in Rats: What is the Mechanism?" Anesthesia & Analgesia, vol. 7, No. 3, pp. 411-415.

Dixon A.K. et al. (1981) "The Effect of DDAVP on Intravenous Urography", British Journal of Radiology, vol. 54, pp. 484-487.

Malan T. Philip et al. (1994) "Subcutaneous Administration of Desmopressin as a Test of Maximal Urinary Concentrating Ability in the Fischer 344 Rat", Toxicology Methods, vol. 4, No. 3, pp. 188-192.

Vilhardt H et al. (1986) "Plasma Kinetics of DDAVP in Man", Acta Pharmacol Toxicol (Copenh), 58 (5): 379-381.

Harris, "Clinical experience with desmopressin: Efficacy and safety in central diabetes insipidus and other conditions," *The Journal of Pediatrics*, vol. 114, No. 4, Part 2, pp. 711-718 (Apr. 1989).

Krishnamoorthy et al., "Prodrugs for nasal drug delivery," *Advanced Drug Delivery Reviews*, vol. 29, pp. 135-146 (1998).

Minirin®—Tablet package information, "Minirin 0.2 mg. Tabletten", (Ferring)(2000), 4 pgs.

Notice of Allowance issued on Feb. 4, 2009 by the Examiner in U.S. Appl. No. 10/513,437 (US 7,560,249).

Office Action issued on Nov. 15, 2007 by the Examiner in U.S. Appl. No. 10/513,437 (US 7,560,249).

Office Action issued on Mar. 27, 2007 by the Examiner in U.S. Appl. No. 10/513,437 (US 7,560,249).

Office Action issued on Apr. 24, 2009 by the Examiner in U.S. Appl. No. 10/513,437 (US 7,560,249).

Office Action issued on Aug. 7, 2008 by the Examiner in U.S. Appl. No. 10/513,437 (US 7,560,249).

Rudnic et al., "Oral Solid Dosage Forms," *Remington: The Science and Practice of Pharmacy*, $20^{th}$ edition, Chapter 45, pp. 858-871, 2000.

International Search Report of EP 03025959.2, dated Oct. 5, 2004.

"Videl 1997", 1997, Editions Du Vidal, Paris XP002277248, p. 1047-1048.

Tormey William Patrick & O'Laoire Sean Arthur (1992) "Severe Prolonged Antidiuresis Following Desmopressin and Carbamazepine Interaction in Postoperative Diabetes Insipidus", European Journal of Internal Medicine, vol. 3, pp. 341-343.0.

U.S. Appl. No. 13/110,619, filed May 18, 2011, Nilsson et al.

"Granulation (making of granules)," http://en.wikipedia.org/w/index.php?title=Granulation_(making_of_granules) &oldid=42594662, accessed on Sep. 13, 2011.

Office Action issued on Aug. 12, 2011 by the Examiner in U.S. Appl. No. 12/224,437 (US 2010/0273709).

Notice of Allowance issued on Apr. 11, 2011 by the Examiner in U.S. Appl. No. 12/487,116 (US 7,947,654).

Law et al., "Stability of Desmopressin Loaded in Liposomes," Journal of Liposome Research, vol. 13, Nos. 3 & 4, pp. 269-277, 2003.

Dobetti, "Fast-Melting Tablets: Developments and Technologies," Pharmaceutical Technology Drug Delivery, pp. 44-50, 2001.

* cited by examiner

BLISTER PACK AND SOLID DOSAGE FORM THEREFOR

FIELD OF THE INVENTION

The present invention relates to a blister pack for pharmaceutical use comprising blisters containing a solid dosage form of desmopressin, or a pharmaceutically acceptable salt thereof, and to said solid dosage form.

BACKGROUND

Desmopressin, also known as dDAVP, is a nonapeptide and the therapeutically active ingredient (as its acetate salt) in the pharmaceutical product Minirin®, which is marketed inter alia as a nasal spray and a tablet formulation. Desmopressin is primarily used in the treatment of primary nocturnal enuresis, i.e. bedwetting, in children, but it is approved also for the treatment of nocturia and diabetes insipidus. The first market introduction of the tablet formulation was in Sweden in 1987. The composition of the marketed tablet form of desmopressin has remained the same to the present date.

The tablet form of desmopressin was first disclosed as set forth in the U.S. Pat. No. 5,047,398. The subsequently issued marketing authorisations relate to a tablet where i.a. the mannitol, talc and cellulose components exemplified in U.S. Pat. No. 5,047,398 are replaced with potato starch. In addition to desmopressin acetate and potato starch, the present tablet components are lactose, polyvinylpyrrolidone (PVP) and magnesium stearate that together form a homogeneous tablet compressed from a granulate. As a mixture of water and ethanol is used as granulation liquid in the granulate preparation, the resulting tablet also contains minor residues of those two solvents, typically 5-6% of water and 0.1% of ethanol (percentage by weight). Complete removal of residual solvents is neither required nor practical, as conditions for complete drying of solid dosage forms tend to be either too costly in industrial scale or potentially thermally damaging to the desmopressin.

A Minirin® tablet has previously been marketed contained in a blister pack comprising polyvinyl chloride (PVC) blisters coated with PVDC (polyvinylidene chloride). An aluminium foil lid provided with a heat seal lacquer was utilised. The blister pack product was withdrawn from the market in 2002 due to a consistent problem with degradation of the desmopressin acetate during long term storage.

The advantages of blister packs compared to a spray or tablets in a bottle are well known. They involve mainly the treating physician's flexibility in selecting a particular number of dosage units and the appearance of the blisters as a practical reminder to the patient of whether a dosage unit has been taken or not. More general guidance on blister packs available for pharmaceutical use is provided in "*Pharmaceutics—The science of dosage form design*"; Ed. M. E. Aulton, Churchill Livingstone, Edinburgh, London, Melbourne and New York, 1988.

There exists a need to provide a blister pack comprising desmopressin that does not suffer from a storage stability problem.

The U.S. Pat. No. 5,763,405 discloses a solid dosage form of desmopressin. It has an enteric coating adapted for providing desmopressin release in the small intestine, and the drug is admixed with a carrier comprising a buffering agent that buffers at a pH from about 2 to about 6. U.S. Pat. No. 5,763, 405 discloses the objective of increasing the desmopressin bioavailability by controlling the gastrointestinal release and ensuing enzymatic degradation of desmopressin.

DISCLOSURE OF THE INVENTION

The present invention relates to a blister pack for pharmaceutical use comprising blisters containing a solid dosage form of desmopressin, or a pharmaceutically acceptable salt thereof, in association with a pharmaceutically acceptable adjuvant, diluent and/or carrier, wherein said solid dosage form is adapted to prevent moisture related degradation of said desmopressin.

The present solid dosage form may optionally comprise at least one further additive typically selected from a disintegrating agent, binder, lubricant, flavoring agent, preservative, colorant and any suitable mixture thereof. Examples of additives that may be considered in practising the present invention are found in "*Handbook of Pharmaceutical Excipients*"; Ed. A. H. Kibbe, $3^{rd}$ Ed., American Pharmaceutical Association, USA and Pharmaceutical Press UK, 2000.

Without being bound by a particular theory, the inventors hypothesise that the presence of residual moisture in solid dosage forms of desmopressin in combination with the increased potential influx of moisture in blister packs (compared e.g. to sealed bottles) caused the aforementioned accelerated degradation of desmopressin upon storage. The presence of moisture in solid dosage forms appears to promote dimer formation, i.e. deactivation, of desmopressin, albeit also other variants of deactivated desmopressin are formed during storage.

More specifically it has been found that a purposive selection and control of the pH level in a solid dosage form of desmopressin is particularly efficient in counteracting degradation upon storage in blister packs.

A preferred embodiment of the present invention relates to said blister pack, wherein said solid dosage form contains an agent that provides a pH in the range of from 3.0 to 6.2 as measured when said solid dosage form is contacted with water. In another embodiment said pH is in the range of from 3.0 to 6.0. As used herein the expression "contacted with water" refers to preparing a slurry of 1 g of a solid dosage form in 2 ml $H_2O$ at 25° C., where the slurry is subjected to a conventional pH measurement. A pH meter of type pHC3359-9 provided by Radiometer Analytical S.A. (France) was utilised for the measurements. A slurry of 1 g of the previously known Minirin® tablet in 2 ml $H_2O$ provides a pH of about 6.6 at 25° C.

It is preferred that said pH is in the range of from 3.5 to 5.5. It is even more preferred that said pH is in the range of from 4.0 to 5.0, preferably from 4.5 to 4.8.

Said agent providing said pH is preferably an acid, preferably an acid selected from a group consisting of citric acid, hydrochloric acid and malic acid. Other examples of suitable acids are stearic acid, acetic acid, phosphoric acid, adipic acid, tartaric acid, glutamic acid and aspartic acid. The possibility of using one substance only as the pH controlling agent makes the present invention particularly convenient to practise.

In the present blister pack said blisters, and also lid foil as suitable, are preferably composed of a material selected from PVC, PVC/PVDC blends, PE (polyethylene), PP (polypropylene), polystyrene, polyester (e.g. a polyester terephthalate), paper, polyamide, PET (polyethylene terephthalate), COC (cyclic olefin copolymer) and aluminium foil or any blend thereof. As used herein the expression "blend" also encompasses a layered composite. PVC is the preferred material.

A typical aluminium blister is made of a blend which is usually a layered composite of oriented polyamide (OPA), aluminium and polypropylene, or PVC, as the bottom web, whereas the lid foil consists of aluminium. The lid foil is typically provided with a heat sealing lacquer for sealing e.g. with the polypropylene. The typical COC blister is made of PP/COC/PP as bottom web, where the aforementioned type of aluminium foil lid may be used. The PVC blister is typically sealed with an aluminium foil lid provided with a conventional heat sealing lacquer adapted for sealing with the PVC. The blister pack manufacturing technology per se utilised in practising the present invention is conventional for a person skilled in the art. Examples of commercial providers are the Alcan Packaging Group (Singen, DE) for aluminium and COC, Riblex Film A/S (Denmark) for PVC and Perlen Converting AG (Switzerland) for PVDC.

In the most preferred embodiment said solid dosage form does not comprise an enteric coating. By entirely avoiding solid dosage forms with an enteric coating the preparation of the solid dosage form is simplified substantially, which is a considerable practical advantage of this particular embodiment.

Said solid dosage form is preferably selected from a group consisting of tablets, granulate powder, lozenge, cachet, dry powder, wafer sheet and capsule. A tablet is most preferred.

A second aspect of the present invention relates to a solid dosage form of desmopressin, or a pharmaceutically acceptable salt thereof, in association with a pharmaceutically acceptable adjuvant, diluent and/or carrier, wherein said solid dosage form comprises an agent that provides a pH in the range of from 4.5 to 5.5 as measured when said solid dosage form is contacted with water; with the proviso that said solid dosage form does not comprise fish gelatin or an enteric coating.

In this second aspect it is preferred that said pH is in the range of from 4.5 to 5.0, preferably from 4.5 to 4.8. Said agent is typically an acid, preferably an acid selected from a group consisting of citric acid, hydrochloric acid and malic acid. Other examples of acids are those previously listed. The solid dosage form as such is preferably selected from a group as previously listed. Tablet is the most preferred alternative.

Accordingly the present invention also relates to a blister pack for pharmaceutical use comprising blisters containing a solid dosage form as defined in the second aspect of the present invention. Said blisters, and lid foil as suitable, are preferably composed of a material selected among those already listed above.

The present pharmaceutical composition in a solid dosage form is typically a perorally available tablet. A tablet may be manufactured by compression of a suitable granulate by procedures well established in the art. Some examples of suitable tablet compressing equipment are rotary presses provided by Elizabeth-Hata International, USA, and Courtoy NV, BE. For a comprehensive overview of pharmaceutical tablet manufacturing, see "*Tableting*" (by N. A. Armstrong) in said "*Pharmaceutics—The science of dosage form design*".

The following examples illustrate the present invention in more detail. They shall not be construed as a limitation of how the invention may be practised.

EXPERIMENTAL

EXAMPLE 1

Preparation of Acid Containing ("Low pH"; 02K24-01) Solid Dosage Form of dDAVP

Lactose (900 g, Pharmatose 150M; provided by DMV, NL) and starch (550 g, AmylSolVät; provided by Lyckeby Stärkelse AB, SE) are mixed and sieved through a 1 mm sieve. A granulation liquid consisting of malic acid (1.88 g), water (75 ml) and PVP (13.8 g, Kollidon® 25; provided by BASF GmbH, DE) is prepared, to which dDAVP (0.75 g; provided by PolyPeptide Laboratories AB, SE) and ethanol (225 g) are added. The granulation liquid is then added to the lactose/starch mixture. After sieving (1.4 mm), drying for 20-25 hours at 40° C. and further sieving (1.4 mm), the obtained granulate is admixed with magnesium stearate (11.3 g, 1.0 mm sieved; provided by Peter Greven NV, NL) and subsequently compressed to 7500 tablets using a single punch tablet compression machine (Fette Exacta 1). A typical prepared tablet containing 0.1 mg of dDAVP is white, convex and oval (6.8×9.6 mm) with a thickness of 3-4 mm and a target weight of 192 mg. It has a smooth surface without scratches or chipped edges, and shows no tendencies to lamination (so-called capping). The residual water content is 6.1% by weight. The pH of a slurry in water of the prepared tablet is 4.6 at 25°. The pH of the dried granulate, i.e. the tablet precursor material which may also be used as a solid dosage form per se, is 4.3.

EXAMPLE 2

Preparation of Acid Free ("Standard pH"; DK7333) Solid Dosage Form of dDAVP

Tablets are prepared as in example 1, albeit the malic acid is omitted. The pH of a slurry in water of the prepared tablet is 6.6 at 25°. The residual water content is 6.1% by weight, i.e. intentionally identical with that of the tablet in example 1.

EXAMPLE 3

Incorporation of the Tablets of Examples 1 and 2 in PVC Blisters and Stability Study A Blister packs are prepared using conventional packaging technology provided by Inpac AB, Lund, SE. PVC blisters (RN23-A, batch #26145-1; provided by Riblex Film A/S) and an aluminium lid foil (K7606002, batch #771297; provided by said Alcan Packaging Group were utilised together with a heat lacquer (Termolack LA723) for sealing.

The blister packages containing the tablets of examples 1 and 2 were stored at 40° C. at a relative humidity (RH) of 75% in climate chambers. The content of water/moisture (% by weight) and intact dDAVP (start content 100% at 0 months) were monitored over time, and the results are summarised in Table 1.

The analytical methods used were conventional Karl Fischer and LC/UV for the water and desmopressin, respectively.

TABLE 1

| | Stability study A | | | | | | | |
|---|---|---|---|---|---|---|---|---|
| Tablet in PVC | dDAVP content (%) months | | | | H$_2$O content (% w/w) months | | | |
| blister | 0 | 1 | 3 | 7 | 0 | 1 | 3 | 7 |
| Ex. 1 | 100 | 92 | 85 | 76 | 6.1 | 7.2 | 8.6 | 8.0 |
| Ex. 2 | 100 | 85 | 66 | 52 | 6.1 | 6.6 | 8.9 | 8.2 |

EXAMPLE 4

Stability Study B of dDAVP Tablets in PVC/PVDC Blisters

The PVDC used is Perlalux-Duplex (batch #39942) provided by Perlen Converting AG, and it coats the PVC blisters as previously mentioned. Aluminium lid foil K7606002 is used.

For comparative purposes a tablet denoted CC6545 is prepared as in example 2, albeit the pH of the tablet when contacted with water is 6.5 due to use of a different batch of potato starch (provided from KMC, Denmark).

Two tablets according to the present invention, otherwise analogous to said CC6545, are prepared by adding acid to the granulation liquid in an amount sufficient to provide a pH of 4.5. Malic acid or hydrochlorid acid are added, and the resulting tablets 45/059 and 45/061, respectively, provide a pH of 6.1 and 6.2, respectively, when contacted with water. Stability tests performed at 40° C./75% RH as in example 3 are summarised in Table 2 below.

TABLE 2

Stability study B

| Tablet in PVC/PVDC blister | dDAVP content (%) months | | |
|---|---|---|---|
| | 0 | 3 | 6 |
| CC6545 (pH 6.5) | 100 | 85 | 76 |
| 45/059 (pH 6.1) | 100 | 88 | 82 |
| 45/061 (pH 6.2) | 100 | 89 | 85 |

In summary, the above results show that a lower pH provides an increased storage stability for a solid dosage form of desmopressin in blister packs.

All references listed are to be regarded as an integral part of the present writ.

The invention claimed is:

1. A blister pack for pharmaceutical use comprising blisters containing a compressed granulate tablet which tablet comprises a compressed granulate comprising:
   desmopressin, or a pharmaceutically acceptable salt thereof;
   an acid that provides a pH in the range of from 3.0 to 6.2 as measured when 1 g of said tablet is slurried in 2 ml of water at 25° C.; and
   a pharmaceutically acceptable adjuvant, diluent or carrier.

2. The blister pack according to claim 1, wherein said acid provides a pH in the range of from 3.5 to 5.5.

3. The blister pack according to claim 2, wherein said acid provides a pH in the range of from 4.0 to 5.0.

4. The blister pack according to claim 1, wherein said blisters are composed of a material selected from the group consisting of: polyvinyl chloride (PVC), polyvinyl chloride/polyvinylidene chloride (PVC/PVDC) blends, polyethylene (PE), polypropylene (PP), polystyrene, polyester, paper, polyamide, polyethylene terephthalate (PET), cyclic olefin copolymer (COC), aluminium foil, and blends thereof.

5. The blister pack according to claim 1, wherein said tablet does not comprise an enteric coating.

6. The blister pack of claim 5, wherein said tablet does not comprise fish gelatin.

7. The blister pack according to claim 6, wherein said blisters are composed of a material selected from the group consisting of: polyvinyl chloride (PVC), polyvinyl chloride/polyvinylidene chloride (PVC/PVDC) blends, polyethylene (PE), polypropylene (PP), polystyrene, polyester, paper, polyamide, polyethylene terephthalate (PET), cyclic olefin copolymer (COC), aluminium foil, and blends thereof.

8. The blister pack according to claim 3, wherein said acid provides a pH in the range of from 4.5 to 4.8.

9. The blister pack according to claim 1, wherein said acid is selected from the group consisting of citric acid, hydrochloric acid, and malic acid.

10. The blister pack according to claim 1, wherein said acid is selected from the group consisting of stearic acid, acetic acid, phosphoric acid, adipic acid, tartaric acid, glutamic acid, and aspartic acid.

11. The blister pack according to claim 1, wherein said compressed granulate tablet comprises desmopressin acetate.

* * * * *